US00PP17722P3

(12) United States Plant Patent
Oud

(10) Patent No.: US PP17,722 P3
(45) Date of Patent: May 15, 2007

(54) ***LOBELIA* PLANT NAMED 'LOBLILACA'**

(50) Latin Name: *Lobelia erinus*
Varietal Denomination: Loblilaca

(75) Inventor: Johannes Simon Nicolaas Oud, Bovenkarspel (NL)

(73) Assignee: Syngenta Seeds B.V., Enkhuizen (NL)

( * ) Notice: Subject to any disclaimer, the term of this patent is extended or adjusted under 35 U.S.C. 154(b) by 52 days.

(21) Appl. No.: 11/223,182

(22) Filed: Sep. 9, 2005

(65) Prior Publication Data

US 2007/0061931 P1 Mar. 15, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers
(74) *Attorney, Agent, or Firm*—Bruce Vrana

(57) ABSTRACT

A new *Lobelia* plant particularly distinguished by its spreading plant habit, strong branching, large flower size and light blue flower color.

1 Drawing Sheet

Latin name of the genus and species of the plant claimed: *Lobelia erinus.*
Varietal denomination: 'Loblilaca'.

BACKGROUND OF THE NEW PLANT

The present invention relates to a new and distinct cultivar of *Lobelia* plant. The new cultivar is propagated by cuttings resulting from the cross between *Lobelia erinus* 'A951-1' and *Lobelia erinus* 'Z868-1.' *Lobelia erinus* 'A951-1' is a blue flower color selection of our own breeding, having a spreading habit, very strong growth, good branching plant habit and being early flowering. *Lobelia erinus* 'Z868-1' is a lilac flower color selection of our own breeding, having a strong growth, trailing plant habit and being early flowering. Neither *Lobelia erinus* 'A951-1' or *Lobelia erinus* 'Z868-1' has been patented.

As a result of this cross the present cultivar was created in 2000 in Enkhuizen, Netherlands and has been repeatedly asexually reproduced by cuttings in Enkhuizen over a four year period. The new variety is stable and reproduces true to type in successive generations of asexual reproduction.

DESCRIPTION OF THE PHOTOGRAPH

This new *Lobelia* plant is illustrated by the accompanying photograph which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Lobelia.* The data, which defines these characteristics, were collected from asexual reproductions carried out in Enkhuizen, Netherlands. The plant history was taken on 20 week old plants.

TABLE 1

DIFFERENCES BETWEEN 'LOBILACA' AND TWO RESEMBLING VARIETIES

| Characteristic | 'Loblilaca' | 'Wesstar' (U.S. Pat. No. PP 12,678) | 'Ricardii' (not patented) |
|---|---|---|---|
| plant | | | |
| height | 20 cm | 25 cm | 25 cm |
| width | 45 cm | 50 cm | 50 cm |
| shape | Spreading to upright | Spreading to upright | Spreading to upright |
| flower color | | | |
| upper surface | N80A | 95B | 95B |
| lower surface | N80B | 100A | 95B |
| flower tube | N80A | 95C | 96D |

No descriptions of parentlines are available. The only info is mentioned as background of the new plant on page 1.

The plant:

*Classification.*—Botanical: *Lobelia erinus.*

*Parentage.*—Female parent: A seeding named *Lobelia erinus* 'A951-1' is one of our seedlings from our A-generation of plants bred in 1999. Male parent: A seedling named *Lobelia erinus* 'Z868-1' is one of our seedlings from our Z-generation of plants bred in 1998.

*Growth habit.*—Spreading to upright.

*Plant height.*—20 cm.

*Spreading area of plant.*—45 cm.

*Growth rate.*—Strong growth.

*Strength.*—Good, excellent.

*Branching character.*—Freely branching and lateral branching at every node. Pinching will enhance branching. Branches strong and flexible.

*Blooming period.*—From May until October.

The stem:

*Diameter.*—1.5 mm.

*Length.*—25 cm.

*Texture.*—Smooth, slightly pubescent, glossy.

*Color.*—RHS 137B in old leaves, RHS 137C in young leaves.

*Length of internode.*—10–20 mm, depending on the light conditions where the plant is grown, and the age of the stem.

*Shape.*—(Tri)angular.

The foliage:

*Shape.*—Leaves simple, generally symmetrical and flat. Broadly ovate with rounded apex, obtuse to attenuate base and crenate margin in young plant; more lanceolate in Mature plant.

*Texture.*—Slightly pubescent on upper and lower sides; very glossy on upper side, glossy on lower side.

*Length.*—25 mm.

*Width.*—In young plant 10 mm, Mature plant 5 mm.

*Color.*—Upper surface: RHS 137B in old leaves, RHS 137C in young leaves. Lower surface: RHS 137B in old leaves, RHS 137C in young leaves.

*Foliage color applies for juvenile as well as mature phase.*—Veins: Pinnate, upper side RHS 137B, lower side RHS 137B.

*Length of petiole.*—Not present in leaves of Mature plant; in young plant up to 10 mm.

*Diameter of petiole.*—20.5 mm.

*Color of petiole.*—RHS 137C.

The flower:

*Type and habit.*—Flower form at apical axils, usually one flower per axil. Flowers labiate, upper lip consisting of two small petals and lower lip consisting of three larger and broader petals. Petals have oblong shape with a mucronulate apex and entire margin.

*Lastingness on the plant.*— 10–14 days depending on temperature. Petals are fused at base into a tube. Freely and continuously flowering, around 100–150 flowers. Flowers face outward.

*Flower.*—Petal Width: Upper petals 1 mm, lower petals 7 mm. Petal length: Upper petals 7 mm, lower peals 9 mm. Flower depth: 17 mm. Flower diameter: 15 mm.

*Texture.*—Smooth, slightly pubescent on upper and lower sides.

*Buds.*—Length: 7 mm. Diameter: 3 mm. Form: Tubular. Color: RHS 144D.

*Flower color.*—Upper surface: RHS N80A. Lower surface: RHS N80B. Flower tube (outside): RHS N80A on upper side, N80C on lower side. On the three lower petals of flower, there is a white spot, width 3 mm, depth 5 mm, color closest to RHS 155D. There is not a white spot on the upper petals. At the base of the lower petals, where the throat starts, there are two yellow markings into the throat (Length 8 mm, width 0.5 mm, RHS 2A).

*Throat.*—Texture: Whiskered. Depth: 8 mm. Diameter: 2.5 mm.

*Throat color.*—RHS 155D with spots of RHS N80A.

*Sepals.*—No. of sepals: 5. Length: 6 mm. Width: 0.5 mm. Texture: Slightly pubescent and glossy for both upper and lower surfaces. Color: RHS 137B upper side and RHS 137B lower side. Shape: Linear. Apex: Acute. Margin: Entire.

Sepals are fused at base.

*Flower stem.*—Length: 20 mm. Angle: Upright. Strength: Rigid, flexible. Color: RHS 137B. Diameter: 0.4 mm.

Reproductive organs:

*Androecium.*—Stamen number: 5. Anther shape: Oblong. Anther length: 2 mm. Anther color: RHS 200A. Pollen color: RHS 9B. Amount of pollen: Moderate.

*Gynoecium.*—Pistil length: 8 mm. Stigma shape: Bilobate. Stigma diameter: 1 mm. Stigma color: N80C. Style color: RHS 77A near stigma, RHS 77A towards base. Ovary color: RHS 137C.

Seed development: Some seed development has been observed on plants of the new *Lobelia*.

*Seed color.*—RHS N199B.

*Seed shape.*—Round.

*Seed size.*—Very small, 'like dust'.

*Seed amount per seed pod.*—Approximately 2000.

Fruit:

*Fruitsize.*—Diameter: 2 mm. Length: 5 mm. Fruit color: RHS 146B.

Disease resistance: No susceptibility or resistance to fungal, bacterial or viral pathogens has been noted.

What is claimed is:

1. A new and distinct variety of *Lobelia* plant, named 'Loblilaca,' as illustrated and described herein.

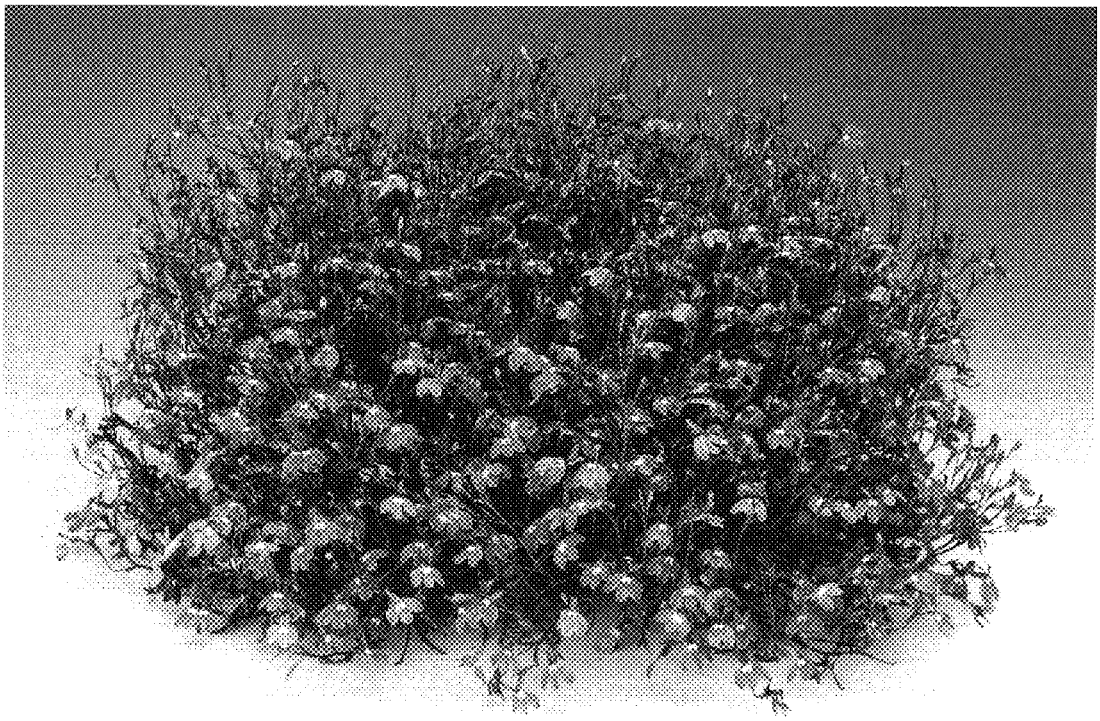

* * * * *